United States Patent [19]

Powell

[11] Patent Number: 4,740,196

[45] Date of Patent: Apr. 26, 1988

[54] NURSING APPARATUS

[76] Inventor: Margaret D. Powell, 315 Oakwood Ave., Salisbury, N.C. 28144

[21] Appl. No.: 88,952

[22] Filed: Jul. 24, 1986

[51] Int. Cl.⁴ .............................................. A61M 1/06
[52] U.S. Cl. ...................................... 604/75; 604/74; 604/346; 128/36; 128/402
[58] Field of Search ................................... 604/73-76, 604/346; 128/34-36.42, 399-403, 24.1-24.5; 119/14.38-14.43, 14.47-14.53

[56] References Cited

U.S. PATENT DOCUMENTS

| 986,738 | 3/1911 | Milligan | 604/74 |
| 2,298,361 | 10/1942 | Freund | 128/402 |
| 3,124,125 | 3/1964 | Jones | 128/36 |
| 3,822,703 | 7/1974 | Davisson | 604/75 |
| 4,323,067 | 4/1982 | Adams | 604/74 |

FOREIGN PATENT DOCUMENTS

| 2807646 | 8/1978 | Fed. Rep. of Germany | 604/74 |
| 533493 | 2/1941 | United Kingdom | 604/74 |
| 660283 | 11/1951 | United Kingdom | 604/74 |
| 2155792 | 10/1985 | United Kingdom | 604/74 |

Primary Examiner—C. Fred Rosenbaum
Assistant Examiner—Mario Costantino
Attorney, Agent, or Firm—Gilden & Israel

[57] ABSTRACT

A nursing apparatus is utilized for stimulating lactation in the female human breast. A breast receiving opening permits the positioning of the apparatus over the female breast, and means for pressurizing and depressurizing an attached chamber then operates to provide a suction action. Additional stimulation is provided by an electrically powered vibrator, while the breast receiving portion includes a chamber which may be filled with warm water to thus simulate the temperature of an infant's mouth.

1 Claim, 2 Drawing Sheets

NURSING APPARATUS

BACKGROUND OF THE INVENTION

1. Field of the Invention

The present invention relates to an apparatus adapted to stimulate lactation, particularly of the female human breast, and more particularly pertains to a nursing apparatus which includes vibration and suction means to enhance stimulation.

2. Description of the Prior Art

The artificial removal of milk from a lactating human breast is generally accomplished by means of a breast pump. Earlier breast pumps usually included a cone-shaped fitting positionable over a breast in an essentially airtight manner along with pumping means such as a rubber bulb to effect a desired suction. However, these earlier pumps usually caused a painful distention of the breast as the milk was removed therefrom.

Later available pumps were designed with the idea of decreasing the amount of pain associated with milk removal. For example, U.S. Pat. No. 3,822,703, which issued to P. Davisson on July 9, 1974, discloses a breast pump wherein the breast receiving opening is fitted with a diaphragm having an aperture large enough for the nipple area to extend therethrough, with the diaphragm being comprised of an elastic material capable of vibrating back and forth in response to the pressurization and depressurization of a chamber when the diaphragm is in engagement with the breast. By permitting only the nipple portion of the breast to extend through the diaphragm, a painful distention of the breast is prevented during a pumping operation. Additionally, the Davisson device recognized the fact that vibratory stimulation will operate to improve lactation. However, the amount of vibratory stimulation provided by a pressurization and depressurization bulb is most likely insufficient to maintain lactation for a prolonged period of time.

A more improved milking apparatus is to be found in U.S. Pat. No. 4,263,912, which issued to F. Adams on Apr. 28, 1981. This device also limits the distention of the human breast to essentially the nipple area, while utilizing two separate pumping bulbs to individually and separately compress the breast and nipple area. This double pumping action is designed to more closely simulate infant nursing. Again however, the amount of stimulation provided by the double pump pumping action is most likely of a minimal amount and further, the Adams device is of a complex construction. Accordingly, the Adams device would be most likely too expensive to manufacture and market.

As can be ascertained from the above discussion of the prior art patents, little or no effort has been directed to the improvement of nursing apparatuses wherein the same could more closely simulate infant nursing. Such improvements should include temperature control, breast receiving orifice shape considerations, and increased vibratory stimulation. In this respect, the present invention substantially fulfills this need.

SUMMARY OF THE INVENTION

In view of the foregoing disadvantages inherent in the known types of nursing apparatuses now present in the prior art, the present invention provides an improved nursing apparatus wherein the same includes breast receiving orifice shape considerations, temperature control, and increased vibratory stimulation. As such, the general purpose of the present invention, which will be described subsequently in greater detail, is to provide a new and improved nursing apparatus which has all the advantages of the prior art nursing apparatuses and none of the disadvantages. To attain this, the present invention comprises a compressible bulb for providing a desired suction action, with a breast receiving orifice operably attached thereto. The breast receiving orifice is designed to be similar in shape to an infant's mouth and includes a surrounding chamber which may be filled with warm water to thus provide temperature control. A vibrator is attached to the bulb and may be adjusted to control the amount of vibration delivered to the breast, while a milk collecting container is attached to a one-way valve assembly forming a part of the bulb.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved nursing apparatus which has all the advantages of the prior art nursing apparatuses and none of the disadvantages.

It is another object of the present invention to provide a new and improved nursing apparatus which may be easily and efficiently manufactured and marketed.

It is a further object of the present invention to provide a new and improved nursing apparatus which is of a durable and reliable construction.

An even further object of the present invention is to provide a new and improved nursing apparatus which is susceptible of a low cost of manufacture with regard to both materials and labor, and which accordingly is then susceptible of low prices of sale to the consuming public, thereby making such nursing apparatuses economically available to the buying public.

Still yet another object of the present invention is to provide a new and improved nursing apparatus which provides in the apparatuses and methods of the prior art some of the advantages thereof, while simultaneously overcoming some of the disadvantages normally associated therewith.

Still another object of the present invention is to provide a new and improved nursing apparatus which includes a breast receiving orifice similar in shape to an infant's mouth.

Yet another object of the present invention is to provide a new and improved nursing apparatus having temperature control means proximate its breast engagement area.

Still even another object of the present invention is to provide a new and improved nursing apparatus which includes additional vibratory stimulation means for stimulating lactation.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENTS

Figure 1:
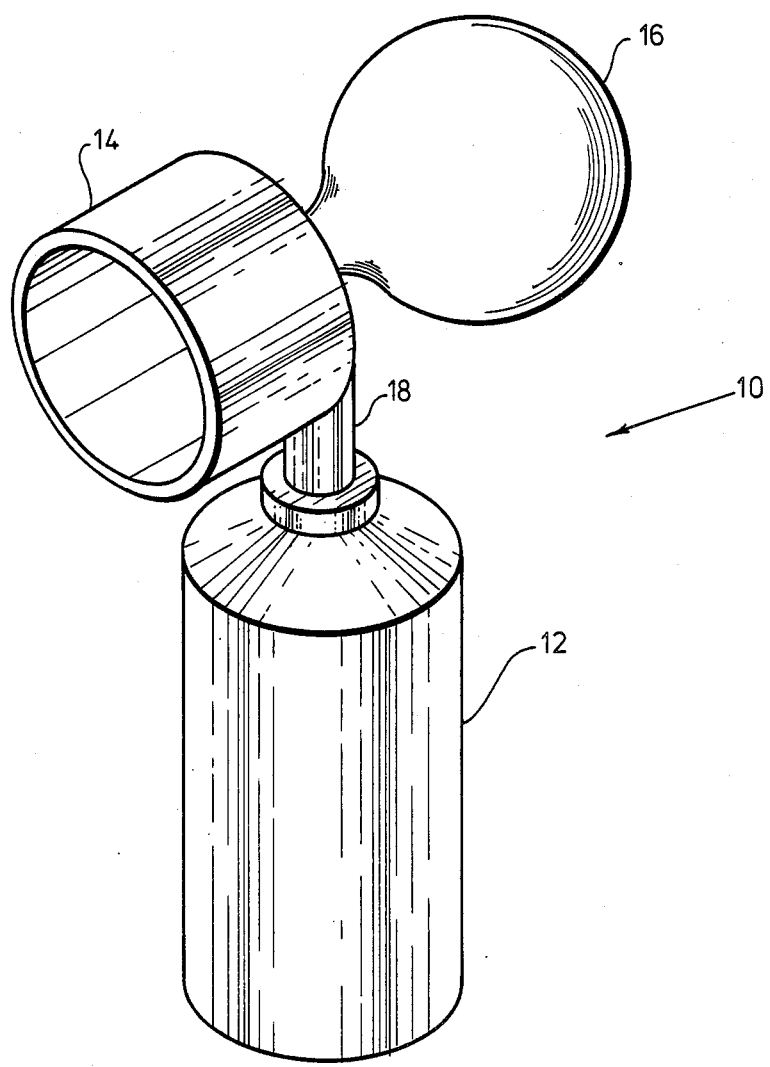
FIG. 1 is a perspective view of the nursing apparatus comprising the present invention.

With reference now to the drawings, and in particular to FIG. 1 thereof, a new and improved nursing apparatus embodying the principles and concepts of the present invention and generally designated by the reference numeral 10 will be described.

More specifically, it will be noted that the nursing apparatus 10 includes a milk receiving container 12 to which is attached a breast receiving assembly 14 and a suction bulb 16. As can be appreciated, the breast receiving portion 14 is designed to be placed over the nipple portion of the female human breast while the section bulb 16 can then be operated to effect a pumping action upon the breast to permit the removal of milk therefrom. The milk is directed to a conduit 18 into the milk receiving container 12.

Figure 3:
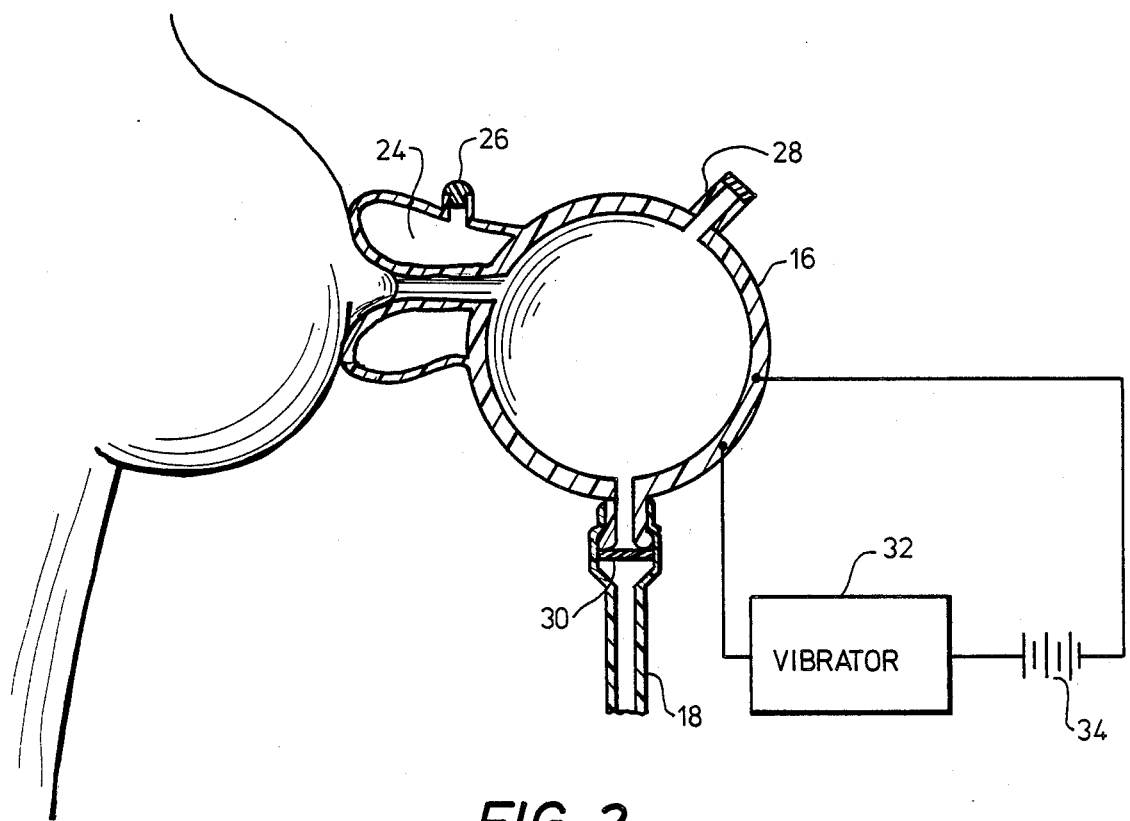
FIG. 3 is a diagrammatic cross-sectional view of the invention showing its various operating components.
Figure 2:
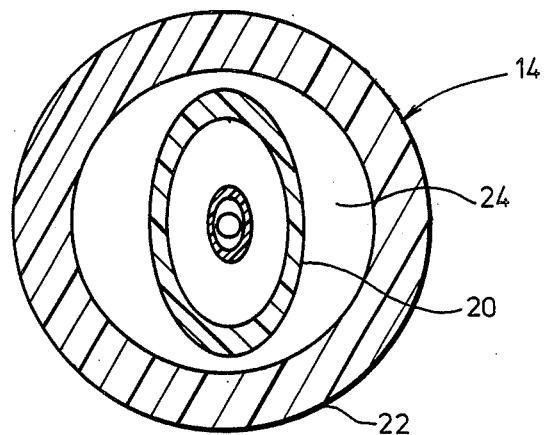
FIG. 2 is a cross-sectional view of the breast engaging orifice forming a part of the invention.

FIGS. 2 and 3 of the drawings illustrate the unique improvements of the present invention over those of the prior art. For example, it will be noted that the breast receiving portion 14 includes an inner nipple engaging section 20 which is designed in the shape of an infant's mouth. Additionally, the breast receiving portion 14 includes an outer breast engaging area 22 with a sealed chamber 24 then being defined by the inner and outer walls 20, 22. An appropriate valve 26 is provided whereby warm water, or the like, can be injected into the chamber 24, thus to control the temperature of the breast receiving portion 14. As such, the mouth shaped section 20, along with the warmth provided with the water in the chamber 24, accurately and efficiently simulates an infant's mouth.

With further reference to FIGS. 2 and 3 of the drawings, it will be noted that the suction bulb 16 is of a conventional design and includes a one-way air ejection valve 28 extending outwardly therefrom. Further, a one-way valve 30 is positioned in the conduit 18 with this valve facilitating the movement of milk through the conduit into the milk container 12, while preventing a reverse flow of the milk from the container into the bulb 16. The valves 28, 30 are of a conventional construction and have been utilized on nursing apparatuses in the prior art. As such, no further discussion thereof appears to be necessitated.

As best illustrated in FIG. 3, a conventional vibrator 32, which is powered by a battery 34 and which includes an appropriate range adjustment means, may be attached in a conventional manner to the suction bulb 16. The vibrator provides a vibratory stimulation to the nipple area of the female breast, thereby to improve the lactation process and more closely simulate the experience of a nursing infant.

With respect to the manner of usage of the present invention, the same should be apparent from the above description. As such, the manner of operation and use of the present invention will not be further described.

With respect to the above description then, it is to realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A nursing apparatus, comprising:

a. milk receiving and collecting means having a substantially cylindrical shape;

b. breast engaging means engageable with a female breast, said breast engaging means having a substantially concave shape, said breast engaging means being fixedly secured to a conduit, said conduit being fixedly secured to and in fluid communication with said milk receiving and collecting means, said breast engaging means including within its concavity a nipple engaging portion, said nipple engaging portion having a substantially ovoid shape to simulate the shape of a baby's mouth;

c. suction bulb in fluid communication with said nipple engaging portion, said suction bulb also being in fluid communication with said conduit, said suction bulb including a one way valve for creating a partion vacuum in said bulb thereby exerting a negative pressure on said nipple for effecting a removal of milk from said breast, said milk travelling through said nipple engaging portion into said suction bulb and from thence through said conduit into said milk receiving and collection means, said milk being prevented from flowing from said milk receiving and collection means into said suction bulb by a one way valve in said conduit means;

d. first stimulation means, said first stimulation means comprising a temperature control means, said temperature control means comprising a warm fluid holding chamber located between an outer and an inner wall of said breast engaging means, said warm fluid holding chamber being filled with a warm fluid to control a temperature of said breast engaging means, said warm fluid being introducible into said fluid holding chamber through a valve fixedly secured to an outer surface of said outer wall of said fluid holding chamber and in fluid communication with said fluid holding chamber; and, e. second stimulation means, said second stimulation means including an electrically powered vibrator operably attached to said suction bulb so as to effect a vibration in said bulb, said vibration being communicated to said nipple engaging portion thereby to simulate the experience of a nursing infant.

* * * * *